US00PP23036P3

(12) United States Plant Patent
Korlipara

(10) Patent No.: US PP23,036 P3
(45) Date of Patent: Sep. 11, 2012

(54) ***ECHINACEA* PLANT NAMED 'SECRET ROMANCE'**

(50) Latin Name: ***Echinacea* spp.**
Varietal Denomination: Secret Romance

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 79 days.

(21) Appl. No.: 12/931,937

(22) Filed: Feb. 14, 2011

(65) Prior Publication Data

US 2012/0210480 P1 Aug. 16, 2012

(51) Int. Cl.
*A01H 5/00* (2006.01)

(52) U.S. Cl. ..... Plt./428

(58) Field of Classification Search ..... Plt./428
See application file for complete search history.

*Primary Examiner* — June Hwu
(74) *Attorney, Agent, or Firm* — Klarquist Sparkman, LLP

(57) ABSTRACT

A new and distinct *Echinacea* plant named 'Secret Romance' characterized by lavender pink ray florets, enlarged deep pink disc florets forming an anemone-type inflorescence, a dwarf habit with good branching and strong stems, and excellent vigor.

1 Drawing Sheet

Botanical denomination: *Echinacea* spp.

Variety designation: 'Secret Romance'.

The present invention relates to a new and distinct cultivar of *Echinacea* and given the cultivar name 'Secret Romance'. *Echinacea* is in the family Asteraceae. This new cultivar is a third generation seeding originating from a planned breeding program using *Echinacea purpurea* 'Razzmatazz' (U.S. Plant Pat. No. 13,894) as the seed parent in the original cross and unnamed proprietary, unreleased interspecific hybrids for the pollen parent. The exact parents of this selection are unknown, unnamed, proprietary plants.

Compared to *Echinacea purpurea* 'Razzmatazz' (U.S. Plant Pat. No. 13,894), the seed parent in the original breeding line, the new variety has a much more compact habit and lighter pink inflorescences.

Compared to *Echinacea* 'Coral Reef' (U.S. Plant Pat. No. 21,888), the new cultivar is much shorter and has lavender pink ray florets rather than dark orange to coral.

Compared to *Echinacea* 'Pink Double Delight' (U.S. Plant Pat. No. 18,803), the new cultivar has more crowns, and a more upright habit, with larger inflorescences that are a different shade of pink.

This new *Echinacea* cultivar is distinguished by:

1. lavender pink ray florets,
2. enlarged deep pink disc florets forming an anemone-type inflorescence,
3. a dwarf habit with good branching and strong stems, and
4. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows *Echinacea* 'Secret Romance' in full bloom as a one-year-old in the field in full sun in July in Canby, Oreg.

DETAILED PLANT DESCRIPTION

The following is a detailed description of the new *Echinacea* cultivar based on observations of a 2-year-old specimens growing in the ground in the trial beds in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, 5$^{th}$ edition.

Plant:

*Type.*—Herbaceous perennial.

*Hardiness.*—USDA Zones 4 to 9.

*Size.*—Grows to about 56 cm wide and 66 cm tall to top of inflorescences.

*Form.*—Basal clump, with about 30 stems from the base.

*Vigor.*—Excellent.

*Roots.*—Fibrous, with many downward growing and few laterals, ivory in color, Yellow White 158D, roots develop easily from cuttings from the crown.

Stem (flowering):

*Type.*—Ascending, with 0 to 5 flowering branches off the main flowering stems.

*Size.*—To 58 cm tall to a terminal inflorescence and 6 mm wide at base.

*Internode length.*—5 cm to 9 cm.

*Surface texture.*—Strigose.

*Color.*—Yellow Green N144A.

Leaf (basal):

*Type.*—Simple.

*Shape.*—Ovate to broadly lanceolate.

*Arrangement.*—Basal.

*Blade size.*—Grows to 10.5 cm long and 5.5 cm wide.

*Margins.*—Sparsely serrate.

*Apex.*—Acute.

*Base.*—Attenuate.

*Surface texture.*—Strigose on both sides.

*Venation.*—Pinnate.

*Color.*—Topside, Green N137A, bottom side closest to Yellow Green 147B.

*Petiole description.*—Grows to 12.5 cm long and 2 mm wide, glabrous, Yellow Green N146C except at base where Red Purple 59A.

Leaf (stem):

*Type.*—Simple.

*Shape.*—Broadly ovate to lanceolate.

*Arrangement.*—Alternate.

*Blade size.*—Grows to 14 cm long and 5.5 cm wide.

*Margins.*—Entire to sparsely serrate.

*Apex.*—Acuminate.

*Base.*—Attenuate.

*Surface texture.*—Strigose on both sides.

*Venation.*—Pinnate, with 3 main veins from the base.

*Color.*—Topside, Green 137A, bottom side closest to Yellow Green 147B.

*Petiole description.*—On lowermost leaves only, clasping, grows to 12 cm long and 4 mm wide above the clasp, strigose, Yellow Green 145A.

Inflorescence:

*Type.*—Composite on terminal stalked heads.

*Number of flowering stems per plant.*—About 30.

*Flowering stem.*—Grows to 58 cm tall from the base of the plant to the terminal inflorescence and can grow to 20 cm long from the top stem leaf to the base of an inflorescence; branched, with 1 to 6 inflorescences per stem; diameter growing to 8 mm wide near the inflorescence; strigose; Yellow Green 146A.

*Size.*—Grows to 9 cm wide and 6 cm deep as disc enlarges.

*Form.*—Ray florets held slightly reflexed, mature disc is conic.

*Immature inflorescence.*—Grows to 3 cm wide and 2 cm deep, ray florets held slightly upright and rolled up so only the back color shows, Greyed Red 182B with Yellow Green N144A on top ¼, disc color two-toned Yellow Green 146C and Greyed Red 182A.

*Ray florets.*—Without pistil or stamen, about 25 in number, grow to 45 mm long and 12 mm wide, oblanceolate with the tip two toothed (each acute), entire margins, base attenuate, glabrous on both sides; topside Purple 75A changing to Greyed Purple 186C on older inflorescences, bottom side closest to Greyed Purple 186C except bottom side tips which are Yellow Green 144A.

*Disc.*—Flat becoming conic, becoming 30 mm deep and 55 mm wide with maturity, overall color is Red Purple 73B lightening to Purple 75B.

*Disc florets.*—About 600 in number, each with 1 pistil and 4 stamen, grow to 26 mm long and 8 mm wide, each with one persistent, very stiff linear bract (8 mm long with the top 2 mm colored Greyed Red 182A on tip then Yellow Green 144A in middle, then White NN155D on bottom ⅓); showy 3 lobed corollas to 24 mm long and 8 mm wide, tubular on the bottom with the lobes spread out like a fan, glabrous on both sides, back side color Greyed Purple 186C, inside color Red Purple 73B; pistil 7 mm long, ovary 3 mm long, White NN155D, style 3 to 5 mm long Red Purple 73D, 2-branched stigma spreading, Greyed Purple 187A; stamen 5 mm long, anthers 2 mm long and Greyed Purple 187A, filaments 3 mm long, Red Purple 73D, very little pollen, Yellow Orange 23B.

*Phyllaries.*—In 4 leafy series, area 3.5 cm wide and 8 mm deep, lobes lanceolate in shape, reflexed, grow to 11 mm long and 4 mm wide, Yellow Green 147B, margins strigose, tip acute, strigose on both sides.

*Receptacle.*—Grows to 12 mm wide and 14 mm deep, White 155A.

*Bloom period.*—July through October in Canby, Oreg.

*Fragrance.*—Excellent, floral.

*Lastingness.*—Each inflorescence lasts about two weeks in Canby, Oreg.

Seeds: 0 to 1 per inflorescence, each 3 mm long and 2.5 mm wide, oval, Brown 200C.

*Fertility.*—Poor.

Disease and pests: *Echinacea* are susceptible to leaf miners, powdery mildew, bacterial spots, and gray mold. None of these have been observed on plants grown under commercial conditions in Canby, Oreg. No resistance is known.

I claim:

1. A new and distinct *Echinacea* plant as herein illustrated and described.

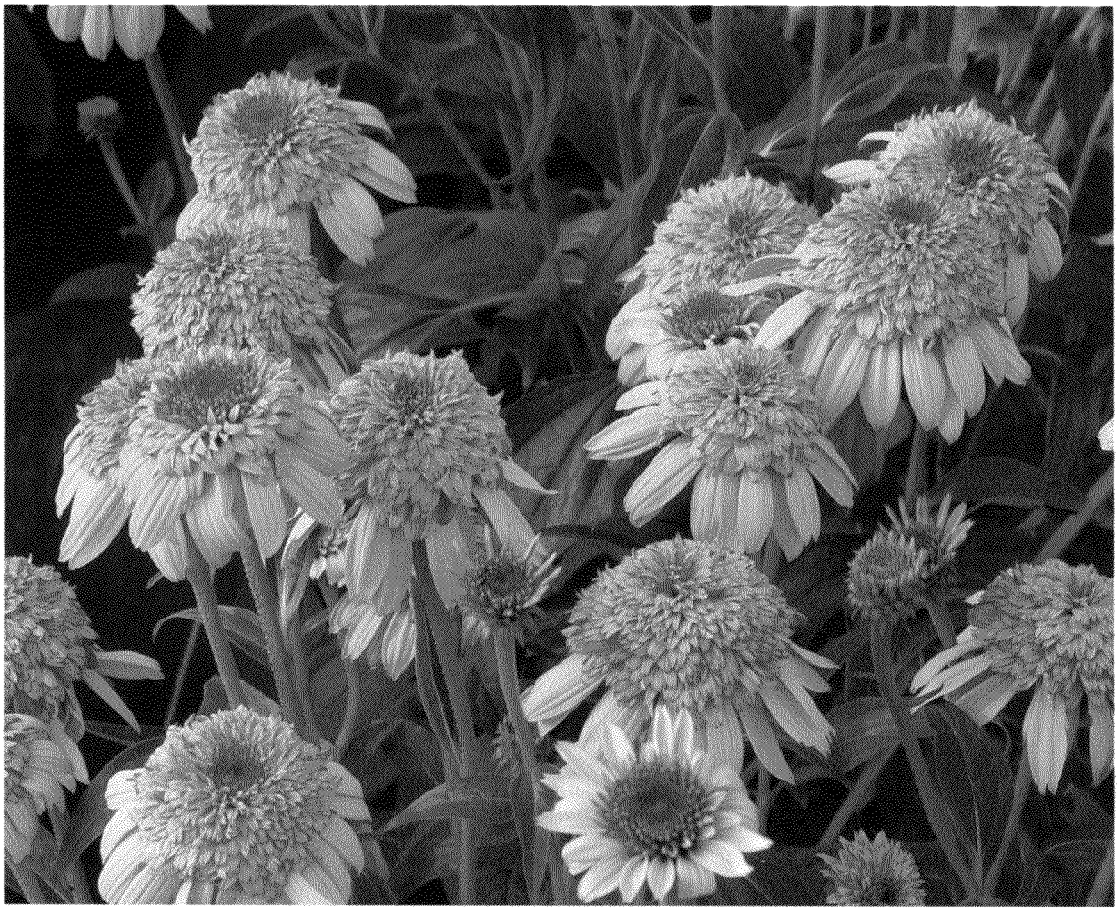

* * * * *